(12) United States Patent
Tanamal et al.

(10) Patent No.: US 6,579,503 B1
(45) Date of Patent: Jun. 17, 2003

(54) STERILIZATION TRAY

(75) Inventors: Linggawati Tanamal, Warsaw, IN (US); Vincent Webster, Warsaw, IN (US); Mark A. Lazzeri, Warsaw, IN (US); Petrus Krafft, Warsaw, IN (US); Verlon C. Caldwell, Jr., Peru, IN (US)

(73) Assignee: Zimmer, Inc., Warsaw, IN (US)

( * ) Notice: Subject to any disclaimer, the term of this patent is extended or adjusted under 35 U.S.C. 154(b) by 339 days.

(21) Appl. No.: 09/660,646

(22) Filed: Sep. 13, 2000

(51) Int. Cl.[7] .............................................. A61L 2/00
(52) U.S. Cl. ....................... 422/300; 206/370; 206/443; 422/297; 606/66; 606/104
(58) Field of Search ............................... 422/300, 297; 206/370, 443; 606/66, 104

(56) References Cited

U.S. PATENT DOCUMENTS 5,099,992 A * 3/1992 Heimreid ..................... 206/366
5,174,453 A * 12/1992 Stoeffler ...................... 206/570
5,525,314 A * 6/1996 Hurson ........................ 422/300
5,681,539 A * 10/1997 Riley .......................... 422/300

OTHER PUBLICATIONS

Prior Art, Zimmer, Inc. Sterilization Tray, Sold on or before 1996.

LCCK Articular Surface Assembly, 1997 Zimmer, Inc. Brochure p. 17–18.

* cited by examiner

Primary Examiner—Krisanne Thornton
(74) Attorney, Agent, or Firm—Jacque R. Wilson

(57) ABSTRACT

An implant sterilization tray includes an integral torquing fixture for holding an implant stationary. By incorporating the fixture into the instrument tray, a large, stable base is provided for holding the implant. The user can more readily hold the implant in a stable position with the implant resting in the case and the case resting on a table.

10 Claims, 3 Drawing Sheets

STERILIZATION TRAY

BACKGROUND OF THE INVENTION

The invention relates to a sterilization tray. More particularly, the invention relates to a sterilization tray having an integral torque fixture.

Surgical instruments are advantageously supplied as modular components that can be assembled at the time of surgery to address the needs of the particular patient. Screws are typically used to attach the components to one another and wrenches are provided to tighten the screws. For example, Zimmer, Inc. sells the NexGen® Complete Knee Solution which includes the Legacy® Knee LCCK components. The tibial component of this knee includes a base plate, an articular surface, and a locking screw to secure the articular surface to the base plate. A tibial plate wrench is supplied for holding the base plate stationary while a second wrench is used to torque the locking screw.

SUMMARY OF THE INVENTION

The present invention provides an alternative to a separate wrench for holding an implant stationary while a screw is torqued into the implant. An implant sterilization tray includes an integral torquing fixture for holding the implant stationary. By incorporating the fixture into the instrument tray, a large, stable base is provided for holding the implant. The user can more readily hold the implant in a stable position with the implant resting in the case and the case resting on a table. It is then only necessary to prevent the case from sliding while the attachment screw is torqued.

DETAILED DESCRIPTION OF THE INVENTION

Figure 1:
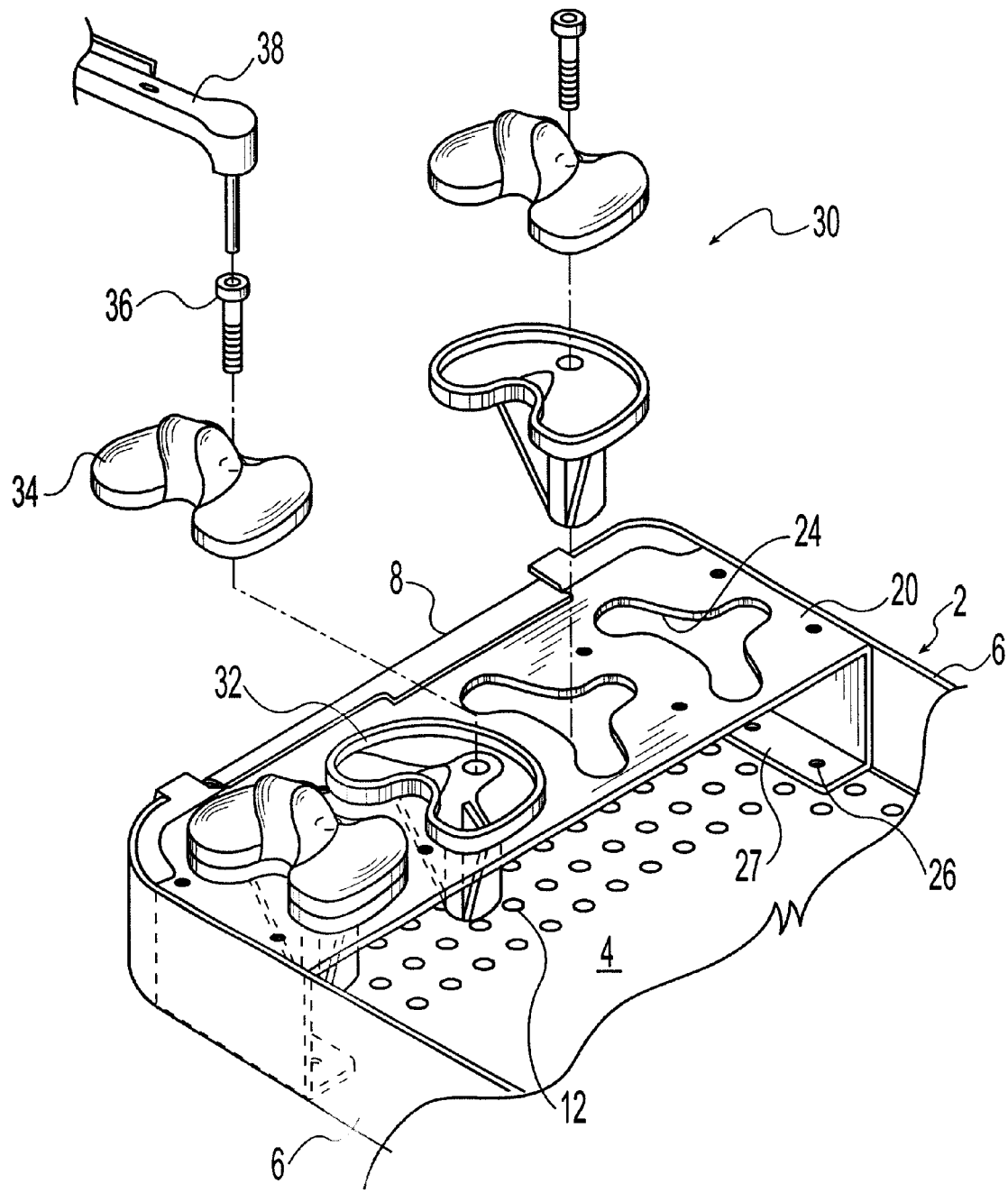
FIG. 1 is a partial perspective view of a torquing fixture incorporated into a sterilization tray according to the present invention.
Figure 2:
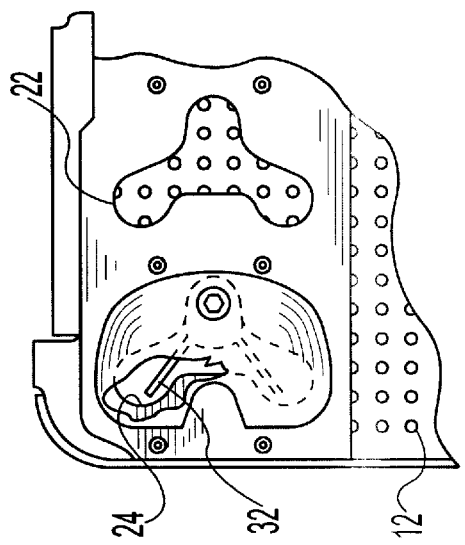
FIG. 2 is a perspective view of the torquing fixture of FIG. 1 separated from the sterilization tray.

FIGS. 1–5 depict an exemplary sterilization tray 2 having a bottom wall 4 and opposing pairs of side walls 6 and 8. A lid 10 is provided to close the open top of the tray. The tray 2 and lid 10 are perforated 12 to let a sterilant, e.g. steam, in and out of the tray 2. Preferably the tray 2, is made of a lightweight, rigid material, e.g. aluminum or aluminum alloy. The lid 10 is preferably made of a transparent, lightweight material, e.g. plastic.

A torquing fixture 20 is incorporated into the tray 2. The torquing fixture 20 includes apertures 22 for receiving an implant to be torqued. Each aperture 22 forms an opening through the torquing fixture and has a peripheral wall 24 defining the aperture 22 shape. The torquing fixture 20 is preferably made of a high strength, non-staining sheet material, e.g. stainless steel. A suitable material is 17-4 stainless steel which is a commonly used stainless steel alloy used for surgical instruments. The torquing fixture 20 is advantageously formed by punching or cutting from the sheet material and then bending to final shape. In one embodiment, the torquing fixture 20 is permanently attached to the sterilization tray 2, e.g. with. rivets 26. In an alternative embodiment, the torquing fixture 20 is removable from the tray 2 so that it can be used separate from the tray 2. In either case, the torquing fixture preferably includes feet 27 for engaging the bottom wall 4 and an edge 28 for engaging side wall 8 to help stabilize the fixture when it is in the tray.

Figure 4:
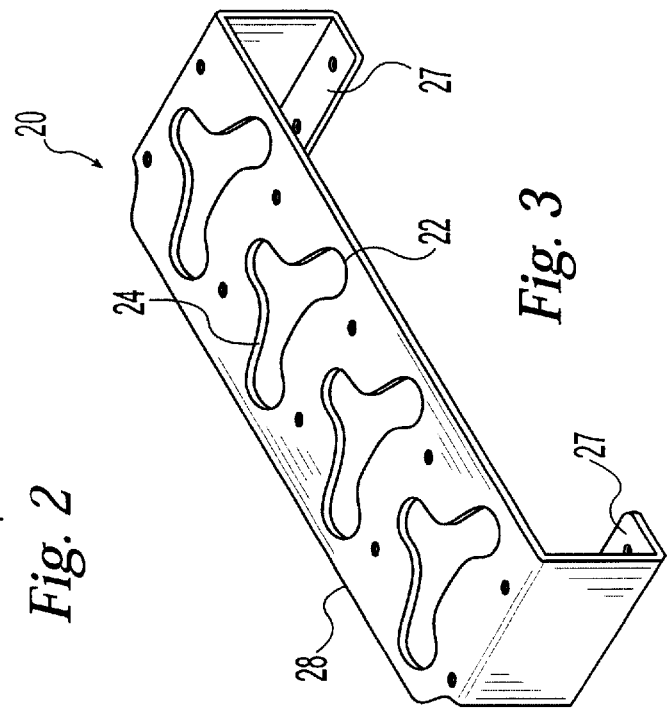
FIG. 4 is a partial top plan view of the torquing fixture of FIG. 1.
Figure 3:
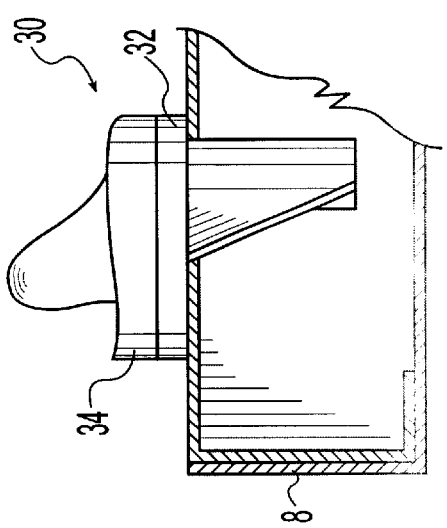
FIG. 3 is a partial side section view of the torquing fixture of FIG. 1 incorporated in a sterilization tray.
Figure 5:
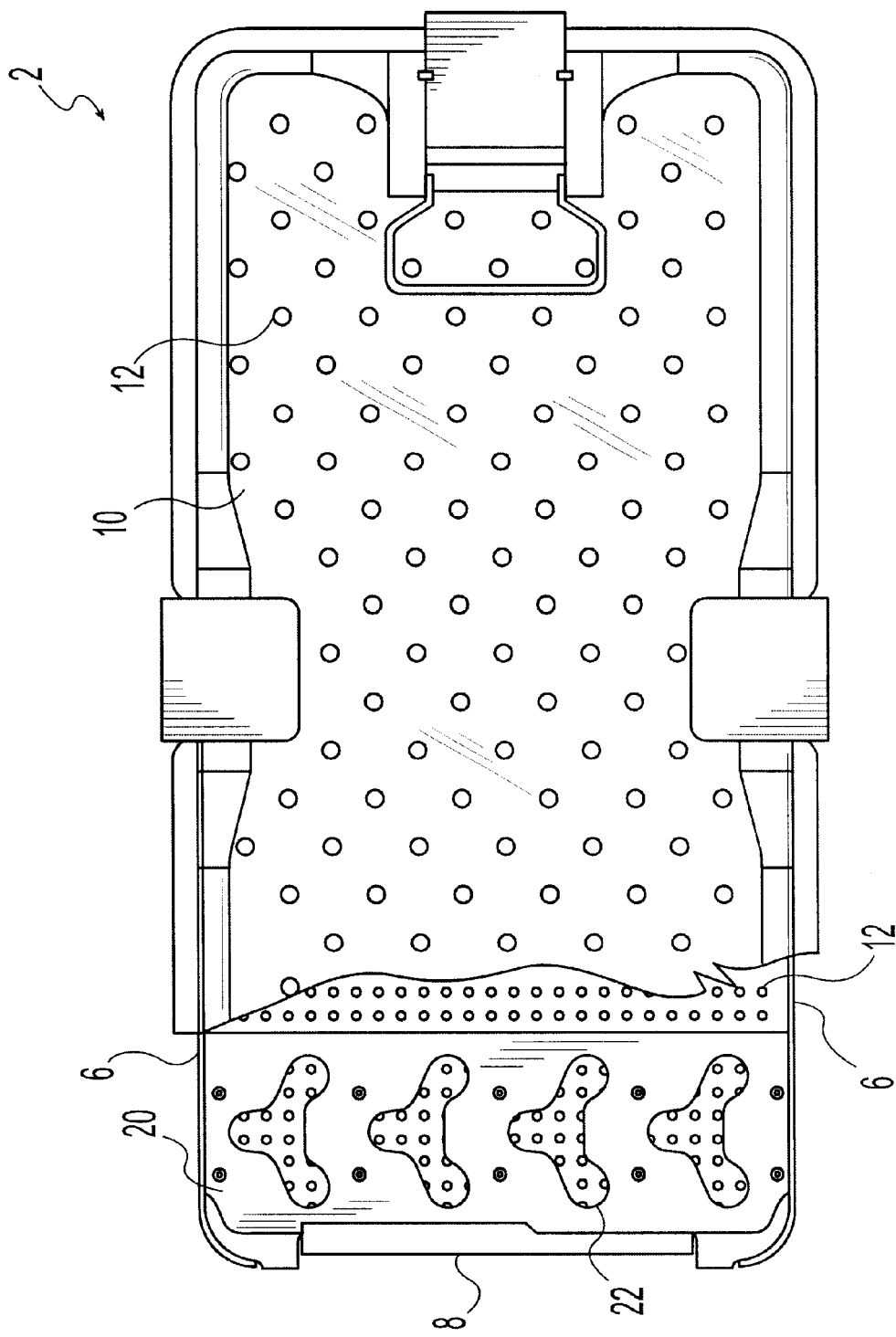
FIG. 5 is a top plan view of the torquing fixture and sterilization tray of FIG. 1.

A modular tibial knee implant 30 includes a tibial base plate 32, an articular surface 34, and a fixation screw 36 for attaching the articular surface 34 to the base plate 32. A torque wrench 38 engages screw 36 for applying a specified torque. Each aperture 22 is sized to receive a different size base plate 32. The aperture 22 receives the base plate 32 in torque transmitting relation such that the peripheral wall 24 positively engages the contours of the base plate 32 to prevent the base plate from turning when the screw 36 is torqued. The material for the torque fixture 20 is chosen to be of sufficient strength, hardness, and gauge that it does not deform or transfer material to the base plate 32 when torque is applied to the implant. Preferably the fit between the aperture 22 and the base plate 32 is such that motion that could lead to scratching or otherwise marring the implant is minimized. Each aperture 22 is advantageously shaped based on the shape of different styles of tibial base plates 32 so that it positively engages each of the different styles of a particular size in the same aperture. For example, the tibial base plate 32 shown is available for a particular size, e.g. size 4, in several different styles or shapes including, e.g. sharp fluted stem, fluted stem, and pegged. The peripheral wall of one aperture 24 is designed to engage each of these styles. The engagement with one style of base plate 32 is shown in FIG. 4. It has been found that a tri-lobed, or clover shaped, design as shown in the figures can be shaped to positively engage each of these styles.

In use, the instrument tray 2 is positioned in the operating room in a convenient location, e.g. a table adjacent the operating table. It typically would contain various instruments used in the implantation procedure. The implantation site for the tibial implant is prepared for receiving the implant as is known in the art. Once the appropriate components have been chosen for the particular patient, they are assembled in the torquing fixture as shown in FIG. 1. The wrench 38 is engaged with the screw 36 and a predetermined torque is applied to the screw 36. The weight of the instrument tray 2 counteracts the torque applied to the screw 36. If further resistance is needed, it is an easy matter to grip the tray 2 or press down on it. The case can also be counter torqued or rotated to counter the applied torque. Because of the relatively large size of the case 2 it is easier to grip and stabilize than the small implant wrenches known in the prior art.

It will be understood by those skilled in the art that the foregoing has described a preferred embodiment of the present invention and that variations in design and construction may be made to the preferred embodiment without departing from the spirit and scope of the invention defined by the appended claims.

What is claimed is:

1. A sterilization tray comprising:
   a bottom wall;
   two pairs of opposing side walls extending upwardly from the bottom wall to form an enclosure interior open at the top;
   a torque fixture attached to the sterilization case interior, the torque fixture having a non-circular aperture for receiving an implant in torque transmitting relation.

2. The sterilization tray of claim 1 wherein the torque fixture includes a plurality of different sized apertures, each aperture for receiving in torque transmitting relation a different sized implant.

3. The sterilization tray of claim 2 wherein each aperture has a peripheral side wall shaped to engage a plurality of different styles of implants of a particular size.

4. The sterilization tray of claim 3 wherein each aperture comprises three lobes, different portions of the three lobes engaging the implant depending on the style of the implant.

5. The sterilization tray of claim 1 wherein the torque fixture includes a top surface containing the aperture and legs depending from the top surface, the legs engaging the bottom wall.

6. The sterilization tray of claim 5 wherein the torque fixture comprises a stamped and folded sheet metal construction.

7. The sterilization tray of claim 6 wherein the torque fixture is made of a stainless steel alloy.

8. A method for torquing an implant, the method comprising the steps of:

provided a sterilization case having a torque fixture attached to the sterilization case interior, the torque fixture having an aperture for receiving an implant in torque transmitting relation;

selecting implant components to be torqued;

placing the components in the torque fixture; and applying a torque to the components.

9. The method of claim 8 further comprising the step of gripping the case to counter the applied torque.

10. The method of claim 8 wherein the torque fixture has a plurality of different sized apertures and further comprising the steps of:

selecting the size of the implant components based on a surgical need;

selecting the style of the implant components bases on a surgical need; and placing the components in a torque fixture aperture corresponding to the size of the selected components.

* * * * *